United States Patent
Smith

(10) Patent No.: US 8,317,382 B2
(45) Date of Patent: Nov. 27, 2012

(54) ENHANCED LED ILLUMINATOR

(75) Inventor: Ronald T. Smith, Irvine, CA (US)

(73) Assignee: Alcon Research, Ltd., Fort Worth, TX (US)

( * ) Notice: Subject to any disclaimer, the term of this patent is extended or adjusted under 35 U.S.C. 154(b) by 51 days.

(21) Appl. No.: 12/960,983

(22) Filed: Dec. 6, 2010

(65) Prior Publication Data

US 2011/0149591 A1    Jun. 23, 2011

Related U.S. Application Data

(60) Provisional application No. 61/289,660, filed on Dec. 23, 2009.

(51) Int. Cl.
*G02B 21/00* (2006.01)

(52) U.S. Cl. ........ 362/555; 362/551; 362/572; 362/573; 362/800

(58) Field of Classification Search .................. 362/800, 362/572, 574, 551, 555
See application file for complete search history.

(56) References Cited

U.S. PATENT DOCUMENTS

| | | |
|---|---|---|
| 4,222,375 A | 9/1980 | Martinez |
| 4,656,508 A | 4/1987 | Yokota |
| 4,870,952 A | 10/1989 | Martinez |
| 4,883,333 A | 11/1989 | Yanez |
| 4,884,133 A | 11/1989 | Kanno et al. |
| 5,086,378 A | 2/1992 | Prince |
| 5,301,090 A | 4/1994 | Hed |
| 5,420,768 A | 5/1995 | Kennedy |
| 5,591,160 A | 1/1997 | Reynard |
| 5,598,042 A | 1/1997 | Mix et al. |
| 5,634,711 A | 6/1997 | Kennedy et al. |
| 5,736,410 A | 4/1998 | Zarling et al. |
| 5,830,139 A | 11/1998 | Abreu |
| 5,859,693 A | 1/1999 | Dunne et al. |
| 6,015,403 A | 1/2000 | Jones |
| 6,036,683 A | 3/2000 | Jean et al. |
| 6,102,696 A | 8/2000 | Osterwalder et al. |
| 6,120,460 A | 9/2000 | Abreu |
| 6,123,668 A | 9/2000 | Abreu |
| D434,753 S | 12/2000 | Druckenmiller et al. |
| 6,183,086 B1 | 2/2001 | Neubert |
| 6,190,022 B1 | 2/2001 | Tocci et al. |
| 6,211,626 B1 | 4/2001 | Lys et al. |

(Continued)

FOREIGN PATENT DOCUMENTS

EP    1114608 B1    3/2003

(Continued)

*Primary Examiner* — Anabel Ton
(74) *Attorney, Agent, or Firm* — Keiko Ichiye

(57) ABSTRACT

An ophthalmic illuminator is disclosed, one embodiment comprising: an illumination source and an optical fiber for transmitting a combined light beam from the illumination source to a site, such as a surgical site within an eye, wherein the illumination source comprises a plurality of light emitting diode (LED) chips optically coupled to a corresponding plurality of light pipes, the LED chips and light pipes arranged in a configuration such that the light pipes converge together at their distal ends to form a cubic box having five sides formed by the distal ends of the light guides and an open side from which the combined light beam, composed of light from a plurality of light beams generated by the LED chips and transmitted to the cubic box by the light guides, is emitted. The luminance of the combined light beam has a luminance greater than the luminance of any one of the plurality of LED chips.

11 Claims, 4 Drawing Sheets

U.S. PATENT DOCUMENTS

| | | | |
|---|---|---|---|
| 6,213,943 B1 | 4/2001 | Abreu | |
| 6,217,188 B1 | 4/2001 | Wainwright et al. | |
| 6,226,126 B1 | 5/2001 | Conemac | |
| 6,270,244 B1 | 8/2001 | Naum | |
| 6,336,904 B1 | 1/2002 | Nikolchev | |
| 6,436,035 B1 | 8/2002 | Toth et al. | |
| 6,730,940 B1 | 5/2004 | Steranka et al. | |
| 6,786,628 B2 | 9/2004 | Steen et al. | |
| 6,893,258 B1 | 5/2005 | Kert | |
| 6,960,872 B2 | 11/2005 | Beeson et al. | |
| 7,025,464 B2 | 4/2006 | Beeson et al. | |
| 7,063,436 B2 | 6/2006 | Steen et al. | |
| 7,229,202 B2 * | 6/2007 | Sander | 362/575 |
| 7,301,271 B2 | 11/2007 | Erchak et al. | |
| 7,325,957 B2 * | 2/2008 | Morejon et al. | 362/555 |
| 7,344,279 B2 | 3/2008 | Mueller et al. | |
| 7,494,228 B2 * | 2/2009 | Harbers et al. | 353/94 |
| 7,556,412 B2 * | 7/2009 | Guillermo | 362/556 |
| 7,682,027 B2 | 3/2010 | Buczek et al. | |
| 2001/0052930 A1 | 12/2001 | Adair et al. | |
| 2002/0087149 A1 | 7/2002 | McCary | |
| 2002/0137984 A1 | 9/2002 | Chhibber et al. | |
| 2003/0132701 A1 | 7/2003 | Sato et al. | |
| 2003/0169603 A1 | 9/2003 | Luloh et al. | |
| 2003/0223249 A1 | 12/2003 | Lee et al. | |
| 2004/0004846 A1 | 1/2004 | Steen et al. | |
| 2004/0090796 A1 | 5/2004 | Steen et al. | |
| 2004/0233655 A1 | 11/2004 | Zimmerman et al. | |
| 2005/0018309 A1 | 1/2005 | McGuire, Jr. et al. | |
| 2005/0024587 A1 | 2/2005 | Somani | |
| 2005/0063171 A1 | 3/2005 | Leitel et al. | |
| 2005/0099824 A1 | 5/2005 | Dowling et al. | |
| 2005/0110808 A1 | 5/2005 | Goldschmidt et al. | |
| 2005/0140270 A1 | 6/2005 | Henson et al. | |
| 2005/0190562 A1 | 9/2005 | Keuper et al. | |
| 2005/0243539 A1 | 11/2005 | Evans et al. | |
| 2006/0262272 A1 | 11/2006 | Anderson et al. | |
| 2007/0273290 A1 | 11/2007 | Ashdown et al. | |
| 2008/0030984 A1 | 2/2008 | Harbers et al. | |
| 2008/0208006 A1 | 8/2008 | Farr | |
| 2008/0246919 A1 | 10/2008 | Smith | |
| 2008/0246920 A1 | 10/2008 | Buczek et al. | |
| 2008/0291682 A1 | 11/2008 | Falicoff et al. | |
| 2009/0036955 A1 | 2/2009 | Han | |
| 2009/0054957 A1 | 2/2009 | Shanbaky | |
| 2009/0095960 A1 | 4/2009 | Murayama | |
| 2009/0105698 A1 | 4/2009 | Hodel et al. | |
| 2009/0154192 A1 | 6/2009 | Krattiger | |
| 2009/0182313 A1 | 7/2009 | Auld | |
| 2009/0190371 A1 | 7/2009 | Root et al. | |
| 2009/0267088 A1 | 10/2009 | Peng et al. | |

FOREIGN PATENT DOCUMENTS

| | | |
|---|---|---|
| JP | 2006087764 A | 4/2006 |
| WO | 00/54655 A1 | 9/2000 |
| WO | 2008/133736 A2 | 11/2008 |

* cited by examiner

ENHANCED LED ILLUMINATOR

This application claims priority to U.S. Provisional Application Ser. No. 61/289,660 filed on Dec. 23, 2009.

TECHNICAL FIELD OF THE INVENTION

The present invention relates generally to the field of illumination systems. In particular, the present invention relates to ophthalmic illumination systems and, more particularly, to a system and method for enhanced LED ophthalmic illumination.

BACKGROUND OF THE INVENTION

Many ophthalmic surgical procedures require illuminating a portion of a patient's eye so that a surgeon can observe the surgical site. Various different types of instruments are known and available for use by an ophthalmic surgeon to illuminate the interior of the eye. Ophthalmic illuminators are commonly used for this purpose.

Ophthalmic illuminators allow a surgeon to illuminate the interior structure of the eye, such as the vitreous and the retina, during surgical procedures. The handheld (probe) portion of a typical ophthalmic illuminator comprises a handle having a projecting tip and a length of optical fiber that enters a proximal end of the handle and passes through the handle and the tip to a distal end of the tip, from which light traveling along the optical fiber can project. The proximal end of the optical fiber can be optically coupled to a light source to receive the light that is transmitted through the fiber. Illuminator probes of this type are typically used by inserting the probe tip through a small incision in the eye. In this way, light from the illuminator light source is carried along the optical fiber, through the handpiece and emitted from the distal end of the probe (fiber) to illuminate the surgical site for the surgeon. In addition to the handheld probe and the light source, a typical ophthalmic illumination system further comprises an enclosure to house the light source and associated optics that guide light from the light source to the optical fiber of the probe, a power supply, electronics with signal processing, and associated connectors, displays and other interfaces as known to those having skill in the art.

Modern small-incision techniques require endo-illuminator probes to have a relatively high-gauge cannula, such as 20 gauge (0.0295 inch diameter) or even higher gauges such as 25 gauge. However, surgeons also require sufficient luminous power from the endo-illuminator to properly illuminate the surgical field within the eye. This is not an issue when a highly luminous source, such as prior art tungsten filament, halogen, and/or high-intensity discharge (HID) bulbs, such as metal halide and xenon bulbs, is used as the endo-illuminator light source because the fraction of the light output from such relatively powerful sources coupled to the fiber is of sufficient luminous power to satisfactorily illuminate a surgical field. But such conventional non-solid-state light sources have many drawbacks when used in an ophthalmic illuminator.

For example, these light sources typically have a short useful lifetime. Because the bulbs and lamps burn out every 300-400 hours, there is a good chance they may burn out during a surgical procedure. Thus, such failures increase the risk of harm to the patient because of the immediate lack of light and the interruption of surgery. The bulb replacement cost is also very high in current ophthalmic endo-illuminators.

Furthermore, these prior art bulbs and lamps generate substantial amounts of heat while consuming substantial amounts of power such that current ophthalmic endo-illuminators have to be made of components capable of withstanding high temperature. Because of the heat produced by the bulbs and lamps used in current ophthalmic illuminators, a cooling fan is typically implemented within the illuminator, which adds to the cost of production/use as well as increases the bulkiness/size of the illuminator. This fan also generates substantial levels of noise in the operating room. In use, these bulbs and lamps take a certain time period to warm up (e.g. tungsten filament to reach thermal equilibrium) during which the color and brightness produced by the ophthalmic illuminator changes.

In contrast, an LED source for an endo-illuminator is much cooler and consumes less power, making it more suitable for use in an operating room environment and, for example, for battery-powered applications. Moreover, an LED source is safer as LEDs are less prone to burning out during surgical procedures as compared to conventional bulb sources. In addition, LEDs are less costly as compared to halogen or HID sources. Although LED light sources thus make an attractive alternative to the conventional use of HID or halogen bulbs, their luminance is typically less than a conventional bulb source. Thus, due to the relatively high etendue of a conventional LED and its relatively low luminance, a conventional LED light source, and particularly single LED light sources, will not pass sufficient light energy into a low etendue optical fiber.

Known methods for attempting to increase the luminance of an LED light source beyond that of a single LED suffer from configuration problems, limited luminance improvement and non-uniformity of the provided light output. For example, one attempt at a solution involves arranging LED's into a cubic shaped configuration with an output aperture at the top of the cube. However, due the constraints imposed by the LED substrate (e.g., thermal management requires a minimum distance between the LED chips) it is not possible to arrange the LED chips close enough to one another to provide a combined output luminance greater than that of a single LED chip. FIG. 2 is a diagrammatical representation of such a prior art arrangement.

Other similar attempted solutions are known. For example, U.S. Pat. Nos. 6,960,872 and 7,025,464 describe high luminance LED scatter boxes comprising multiple LEDs arranged inside of a box, the interior coated with high reflectance diffusive material, and the box having an exit port for the combined LED output light. The described approaches have exit ports having a reduced area compared to the emitting area of the individual LEDs. While the resulting devices may be capable of increased luminance over that of a single LED, the less than 100% reflectance of the diffuse reflective surface of the inside of the scatterbox limits the amount of luminance improvement possible. Further, some view angles looking back into the scatterbox through the exit port will orient directly at an LED-emitting surface, which has a higher luminance than that of the diffuse surface of the box adjoining the LED. The resultant angular luminance non-uniformities of the light emitted from the exit port are not desirable in certain applications, such as for illumination of ophthalmic procedures.

Therefore, a need exists for a method and system for enhanced LED ophthalmic illumination that can reduce or eliminate the problems of prior art ophthalmic illumination systems discussed above, including increasing the luminance of an LED light source to provide sufficient luminous power to a surgical site without increasing the LED current, which typically would result in more dissipated electrical power and more problematic thermal management issues.

BRIEF SUMMARY OF THE INVENTION

The embodiments of the method and system for enhanced LED ophthalmic illumination of this invention substantially meet these needs and others. One embodiment of the present invention is an ophthalmic illuminator comprising: an illumination source and an optical fiber for transmitting a combined light beam from the illumination source to a site, such as a surgical site within an eye, wherein the illumination source comprises a plurality of light emitting diode (LED) chips optically coupled to a corresponding plurality of light pipes, the LED chips and light pipes arranged in a configuration such that the light pipes converge together at their distal ends to form a cubic box having five sides formed by the distal ends of the light pipes and an open side from which the combined light beam, composed of light from a plurality of light beams generated by the LED chips and transmitted to the cubic box by the light guides, is emitted. The luminance of the combined light beam has a luminance greater than the luminance of any one of the plurality of LED chips.

The LED light chips can be high-powered LED chips as will be known to those having skill in the art. The light pipes can be square solid light pipes. The light source can further comprise a mirror, the reflecting surface facing in towards the interior of the cubic box, at the open side of the cubic box; and/or a supporting structure to position and hold in place the plurality of LED chips and light pipes. In a preferred embodiment, five LED chips and five corresponding light pipes are arranged such that each square light pipe and LED pair is orthogonal to the others. The supporting structure in such an embodiment can comprise a cubical structure in which the five LED chips and corresponding light pipes are arranged in the interior of the cubical structure such that an LED chip is positioned substantially centered on each interior wall of the cubical structure. The light pipes optically coupled to the LED chips will thus converge substantially near the center of the cubical structure, as shown in FIG. 1, to form the cubic box. Alternatively, the supporting structure can be any supporting structure that can be used to position and hold in place the LED chips and light pipes in such a configuration.

The ophthalmic illuminator can also comprise a coupling optical component, optically coupled to the plurality of light pipes, for transmitting the combined light beam from the cubic box open side to the optical fiber, or to an intermediary target, and a connector port for coupling the ophthalmic illuminator to an endo-illuminator probe, the probe comprising a connector, a handpiece housing an external optical fiber and a probe tip for carrying the external optical fiber into the surgical site. The connector can be attached (and detached) to the connector port for aligning the light exiting the light source with the external optical fiber.

Other embodiments of the present invention can include a method for enhanced LED ophthalmic illumination and a system for enhanced ophthalmic illumination comprising an ophthalmic illuminator as described above and one or more illuminator probes and supporting devices, such as a user interface and control devices.

Embodiments of this invention can be implemented within a surgical machine or system for use in ophthalmic or other surgery. In particular, it is contemplated that the method and system for enhanced LED illumination of this invention can be implemented in, or incorporated into, any ophthalmic illumination system in which it is desirable to efficiently couple the light from an LED light source to a small diameter optical fiber. Other uses for the method and system of this invention will be apparent to those having skill in the art.

BRIEF DESCRIPTION OF THE SEVERAL VIEWS OF THE DRAWINGS

A more complete understanding of the present invention and the advantages thereof may be acquired by referring to the following description, taken in conjunction with the accompanying drawings, in which like reference numbers indicate like features and wherein.

DETAILED DESCRIPTION OF THE INVENTION

Preferred embodiments of the present invention are illustrated in the figures, like numerals being used to refer to like and corresponding parts of the various drawings.

The various embodiments of the method and system for enhanced LED illumination of this invention provide an LED illumination source capable of providing light with luminance greater than the luminance of a single LED chip and efficiently coupling the light to a small diameter target, such as an optical fiber. One embodiment of the present invention is an ophthalmic illuminator comprising: an illumination source and an optical fiber for transmitting a combined light beam from the illumination source to a site, such as a surgical site within an eye, wherein the illumination source comprises a plurality of light emitting diode (LED) chips optically coupled to a corresponding plurality of light pipes, the LED chips and light pipes arranged in a configuration such that the light pipes converge together at their distal ends to form a cubic box having five sides formed by the distal ends of the light pipes and an open side from which the combined light beam, composed of light from a plurality of light beams generated by the LED chips and transmitted to the cubic box by the light guides, is emitted. The luminance of the combined light beam has a luminance greater than the luminance of any one of the plurality of LED chips.

Figure 1:
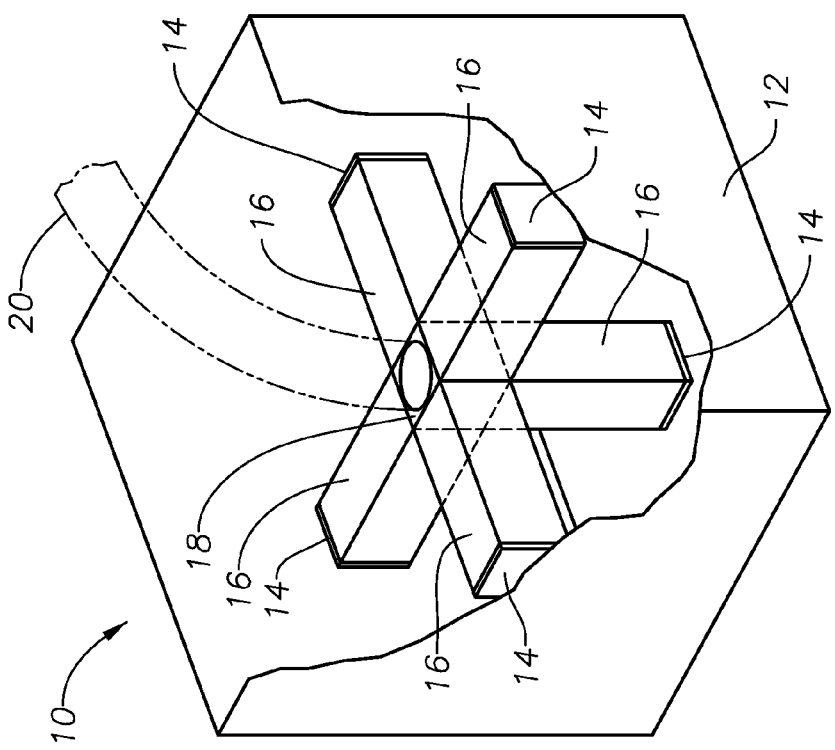
FIG. 1 is a diagrammatical representation of one embodiment of a light source for enhanced LED illumination of the present invention.

The LED light chips can be high-powered white LED chips as will be known to those having skill in the art. The light pipes can be square solid light pipes. The light source can further comprise a mirror, the reflecting surface facing in towards the interior of the cubic box, at the open side of the cubic box; and/or a supporting structure to position and hold in place the plurality of LED chips and light pipes. In a preferred embodiment, five LED chips and five corresponding light pipes are arranged such that each square light pipe and LED pair is orthogonal to the others. The supporting structure in such an embodiment can comprise a cubical structure in which the five LED chips and corresponding light pipes are arranged in the interior of the cubical structure such that an LED chip is positioned substantially centered on each interior wall of the cubical structure. The light pipes optically coupled to the LED chips will thus converge substantially near the center of the cubical structure, as shown in FIG. 1, to form the cubic box. Alternatively, the supporting structure can be any supporting structure that can be used to position and hold in place the LED chips and light pipes in such a configuration.

The ophthalmic illuminator can also comprise a coupling optical component, optically coupled to the plurality of light pipes, for transmitting the combined light beam from the cubic box open side to the optical fiber, or to an intermediary target, and a connector port for coupling the illumination source to an endo-illuminator probe, the probe comprising a connector, a handpiece housing an external optical fiber and a probe tip for carrying the external optical fiber into the surgical site. The connector can be attached (and detached) to the connector port for aligning the light exiting the light source with the external optical fiber.

FIG. 1 is a diagrammatical representation of one embodiment of a light source for enhanced LED illumination of the present invention. Light source 10 comprises five LED chips/LED substrates 14 and five corresponding light pipes 16 arranged such that each square light pipe and LED pair is orthogonal to the others. Supporting structure 12 in this embodiment is a cubical structure for positioning and holding in place LED chips 14 and light pipes 16. LED chips 14 and light pipes 16 are arranged in the interior of support structure 12 such that an LED chip 14 is positioned substantially centered on each interior wall of support structure 12. Light pipes 16 are optically coupled to the LED chips 14 and are shaped and dimensioned such that they converge substantially near the center of supporting structure 12 to form a cubic box having five sides formed by the distal ends of the light guides 16, and an open side. Light pipes 16 can be solid, square dielectric light pipes made of glass or plastic, as will be known to those having skill in the art.

When powered, LED chips 14 each generate and emit light. Each light pipe 16 is optically coupled, e.g., by bonding with optical adhesive or other such bonding technique as will be known to those having skill in the art, to a corresponding LED chip 14. The light emitted by each LED chip 14 is efficiently coupled into a corresponding light pipe 16 and propagates towards the distal end of each light pipe 16 by total internal reflection with nearly 100% efficiency. In transmitting a light beam emitted by an LED chip 14 from its proximal end to its distal end, each light pipe 16 preserves the etendue—the product of the emitting area of the LED chip 14 and the solid angle—of the light beam. Therefore, the luminance of the light emitted from the distal end of a light pipe 16 is essentially equivalent to the luminance of the light at the exit face of the bare LED chip 14 at the light pipe's proximal end. Therefore, the light pipes 16 virtually move an LED chip's 14 emitting surface to the light pipe 16 distal end face. Thus, a virtual LED emitting surface with luminance nearly equal to the luminance at the surface of an actual LED chip 14 exists at the distal end face of each light pipe 16 and as a result for an observer looking back into the open face of the cubic box formed by the convergence of the distal ends of the light pipes 16, at any viewing angle an emitting LED chip 14 surface is visible at the distal end face of each light pipe 16.

Each light ray emitted from each light pipe 16's distal end will either exit the light source 10 through the cubic box open side, reflect off of a dielectric/air interface at the distal end face of one of the other four light pipes 16, or enter via refraction into a distal end face of one of the other four light pipes 16. Light rays that exit one light pipe 16 and enter another light pipe 16 will propagate via total internal reflection with nearly 100% efficiency to the proximal end of the second light pipe 16, efficiently pass through the bonding adhesive between the second light pipe 16 proximal end and its corresponding LED chip 14 and impinge on the LED chip 14. These light rays are then either absorbed by the LED chip 14 or are diffusely reflected by the LED chip 14 back into the light pipe 16. Up to about 85% of the light incident on an LED chip 14 in this way will be reflected back into the respective light pipe 16, propagate down the light pipe 16 to the distal end face and exit into the cubic box.

In this manner the effective luminance (luminous flux/area/projected solid angle) of each virtual LED chip 14 at the distal end face of each light pipe 16 is significantly higher than the luminance of a single LED chip 14 in isolation. Due to absorbance losses of light in each LED chip 14, the resultant overall luminance provided by the five light pipes 16 is significantly less than five times the luminance of a single LED chip 14 in isolation. However, the overall luminance increase is substantial—about 1.5 to 1.6 times the luminance of a single LED chip 14. The combined light thus provided by the light pipes 16 at the cubic box, and which is emitted from the light source 10 at the open side of the cubic box formed by the convergence of the distal ends of the light pipes 16, therefore is emitted with an enhanced luminance as described above and herein.

Further, the LED chips 14 can be selected to be Lambertian emitters (constant luminance in all directions), which most high power LED chips are. If so, the light emission at the distal end face of each light pipe 16 will be essentially Lambertian as well. Therefore, from the vantage point of an observer looking back into the cubic box through the cubic box open side, the same constant luminance is observed from all directions and the light emitted from the light source 10 via the open side of the cubic box will be Lambertian as well. The lack of intensity non-uniformities with angle at the exit aperture of the light box—the open side of the cubic box—is an advantage of the embodiments of the present invention over prior art illuminators.

Figure 1A:
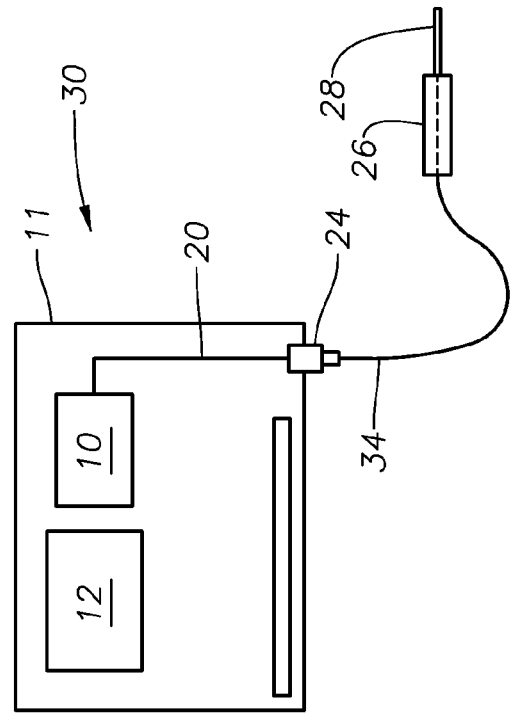
FIG. 1A is a diagrammatical representation of an embodiment of an enhanced LED illumination system of the present invention.

FIG. 1A is a diagrammatical representation of an embodiment of an enhanced LED illumination system of the present invention. Illumination system 30 comprises a power supply 12 and illumination source 10, which can be an illumination source 10 of the embodiment of FIG. 1, optical component 20 and optical fiber port 24. Illumination system 30 also can comprise one or more optical fiber probes 26 for receiving and transmitting light from illumination source 10 to a surgical site. Optical fiber probes 26 comprise the handheld portion of the illuminator system 30, including external optical fiber 34, which is optically coupled to the illumination source 14 within enclosure 11. Optical fiber probes 26 further comprise a probe tip 28, which can be a hollow cannula, for housing and directing external optical fiber 34 to deliver the light from illumination source 10 to a site, such as a surgical site. Enhanced LED illumination system 10 is exemplary only and is not intended to limit the scope of the present invention in any way. The embodiments of the present invention can be used to enhance any such ophthalmic illuminator or any other system or machine in which it is desirable to provide LED illumination of a site.

Although illumination system 30 is shown comprising a single optical fiber port 24 (which can comprise aspheric lenses or other focusing elements), it will be known to those having skill in the art that either a single optical port 24 or multiple optical ports 24 can be implemented within illumination system 30. Illumination system 30 further comprises a printed circuit board ("PCB") 35, or its electronic equivalent, to provide signal processing and control functions. PCB 35 can be implemented in any manner and configuration capable of performing the desired processing and control functions described herein, as will be apparent to those having skill in the art. Optical port 24 comprises a receptacle to receive the proximal end of an external optical fiber 34 corresponding to a fiber probe 26, which is inserted into the illuminator enclosure 11 and optically coupled to illumination source 10 via optical component 20 to direct light onto a desired site. Optical component 20 can be an optical fiber, light guide or other optical element to optically couple the output of illumination source 10 to an optical probe 26 or other device, as will be described more fully below. In some embodiments, optical component 20 is not present as illumination source 10 can be coupled directly to optical port 24. In such embodiments, for example, the open side of the cubic box of illumination source 10 (i.e., the output port of illumination source 10) can be optically coupled directly at optical port 24 to, for example, optical fiber probe 26. In other embodiments, optical component 20 can be coupled to the illumination source 10 at a proximal end and to an external device (e.g., optical fiber probe 26) at its distal end via optical port 24.

Returning now to FIG. 1, if a target to be illuminated (e.g., optical component 20 or external optical fiber 34 of optical fiber probe 26) has a square cross-sectional input face having the same side dimensions as an LED chip 14/light pipe 16, then either the target can be coupled to illumination source 10 directly at the open side of the cubic box, or a square solid dielectric or a hollow reflective light pipe can be coupled to illumination source 10 at the open side of the cubic box to transmit the combined light output from illumination source 10 to the target. For example, in the latter case, optical component 20 can be a square solid dielectric or a hollow reflective light pipe coupled to illumination source 10 as described above at its proximal end to transmit light from illumination source 10 to optical port 24 and then to a square-faced target. Such an embodiment is shown in FIG. 3.

Figure 3:
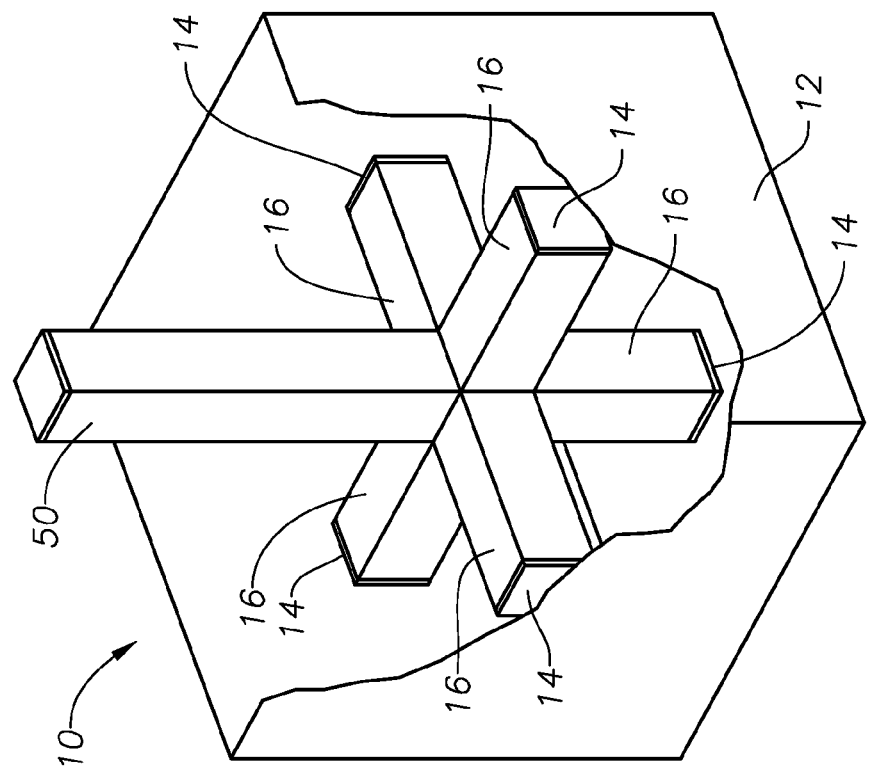
FIG. 3 is a diagrammatical representation of an embodiment of the light source of the present invention comprising a coupling light pipe for optically coupling the output of the light source to a square target.
Figure 2:
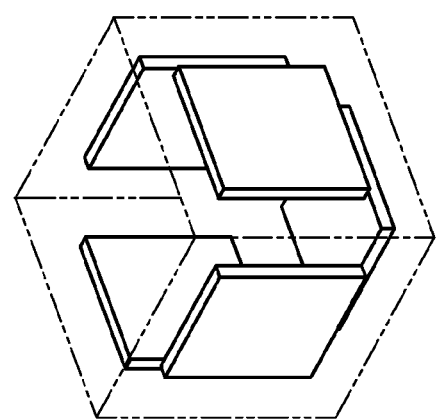
FIG. 2 is a diagrammatical representation of a prior art LED illumination arrangement.

FIG. 3 is a diagrammatical representation of an embodiment of the light source 10 of the present invention comprising a coupling light pipe 50 for optically coupling the output of illumination source 10 to a square target as described above. In this embodiment, coupling light pipe 50 has a proximal end that converges with the distal ends of the five light pipes 16 such that together the five light pipe 16 distal end faces and the coupling light pipe 50 proximal end face form the six sides of the cubic box described above with reference to FIG. 1. The proximal end face of coupling light pipe 50 is thus co-incident with the open side of the cubic box of FIG. 1.

If it is desired to couple the output light from illumination source 10 to a square target having different side dimensions (e.g., smaller side dimensions) than an LED chip 14/light pipe 16, than coupling light pipe 50 can be tapered instead of having a constant square cross-section. Depending on the intended application, the ideal taper shape for coupling light pipe 50 can be a square or a cross two-dimensional compound parabolic concentrator (CPC) shape as described in Chapters 4 and 5 of *Nonimaging Optics*, Roland Winston et al., Elsevier Academic Press, Burlington, Mass., 2005. However, the CPC shape can also be approximated as a linear taper while maintaining very good luminance preservation. Alternatively, instead of having a tapered coupling light pipe 50, a taper can instead be implemented in each of the five light pipes 16 of illumination source 10. In such an embodiment, the illumination target can be coupled directly to the exit aperture (the open side of the cubic box formed by the convergence of the five light pipes 16) of illumination source 10.

Figure 4A:
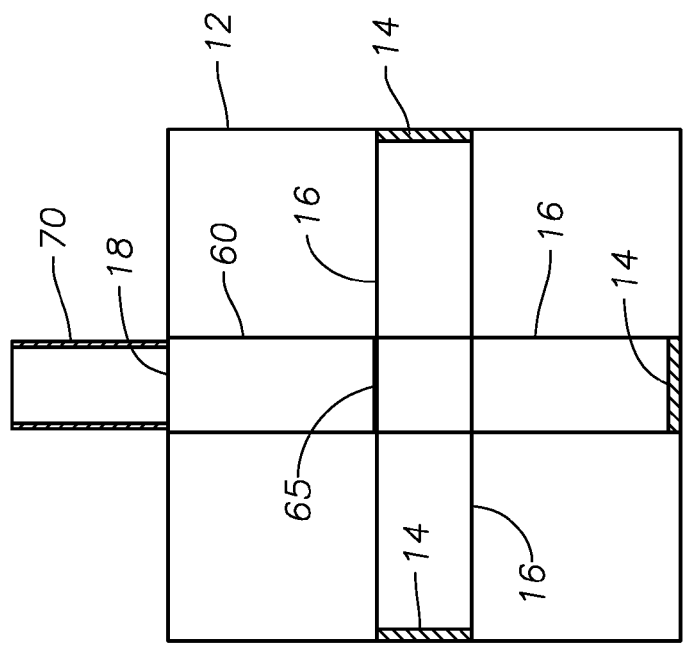
FIG. 4 is a diagrammatical representation showing perspective and side views of an embodiment of a light source of the present invention comprising a coupling light pipe having a spectral coating at its proximal face and a mirror at its distal face.
Figure 4:
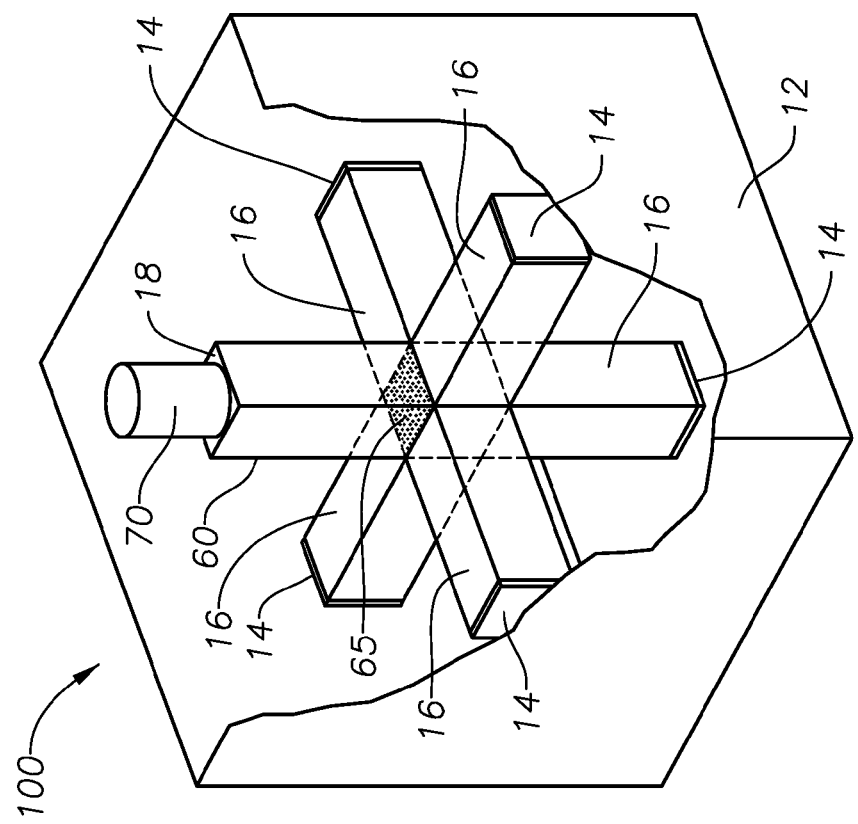

If it is desired to couple the output light from illumination source 10 to a circular target, such as an optical fiber, having a fiber core diameter equal to the side dimensions of an LED chip 14/light pipe 16, then illumination source 10 can further comprise a square reflective mirror 18 having a centered circular opening as shown in FIGS. 1 and 4 positioned at the open side of the cubic box. An optical fiber target can then be optically coupled to the light source 10 at the mirror circular opening. The mirror 18 is positioned such that its reflective surface faces into the cubic box of illumination source 10 and can thus reflect back into illumination source 10, with near 100% efficiency, light rays that spatially fall outside of the mirror 18 circular opening and that hence do not impinge on the face of the optical fiber coupled to the illumination source 10. A significant portion of these reflected light rays will eventually exit light source 10 and enter the optical fiber entrance face per the process described above with reference to FIG. 1 regarding the interaction of light rays in the light pipes 16 and LED chips 14. Mirror 18 can thus cause light rays that would otherwise be wasted to be recycled. In some embodiments, the cubic box formed by the converging distal faces of the light pipes 16 can be filled by a dielectric cube. The dielectric cube can provide a surface on which to mount mirror 18. Alternatively, the mirror 18 circular opening (aperture) can be coated onto an output face of such a dielectric cube, the output face being the cube face not coupled to a light pipe 16. In still a different embodiment, a reflective mirror can be a part of the circular illumination target; for example, the proximal face of an ACMI connector into which an optical fiber is mounted.

If a circular illumination target as described above instead has a diameter different from the side dimensions of an LED chip 14/light pipe 16, the light pipes 16 of the illumination source 10 can be appropriately tapered to efficiently couple the illumination source 10 output light to the illumination target. Alternatively, a tapered circular light pipe, analogous to coupling light pipe 50 of FIG. 3, can be used to couple illumination system 10 to the circular illumination target.

FIG. 4 is a diagrammatical representation showing perspective and side views of an embodiment of a light source 100 of the present invention comprising a coupling light pipe 60 having a spectral coating 65 at its proximal (input) face and a mirror 18, as described above, at its distal face for coupling the combined light output from light source 100 (as provided by LED chips 14 and light pipes 16) to an illumination target 70 (e.g., an optical fiber having a circular cross-section). Coupling light pipe 60 can be a square dielectric light pipe with spectral coating 65 co-incident with the distal faces of light pipes 16 as shown. Embodiments of the light source 100 can comprise interchangeable coupling light pipes 60 with different spectral coatings selected for particular applications.

Figure 5:
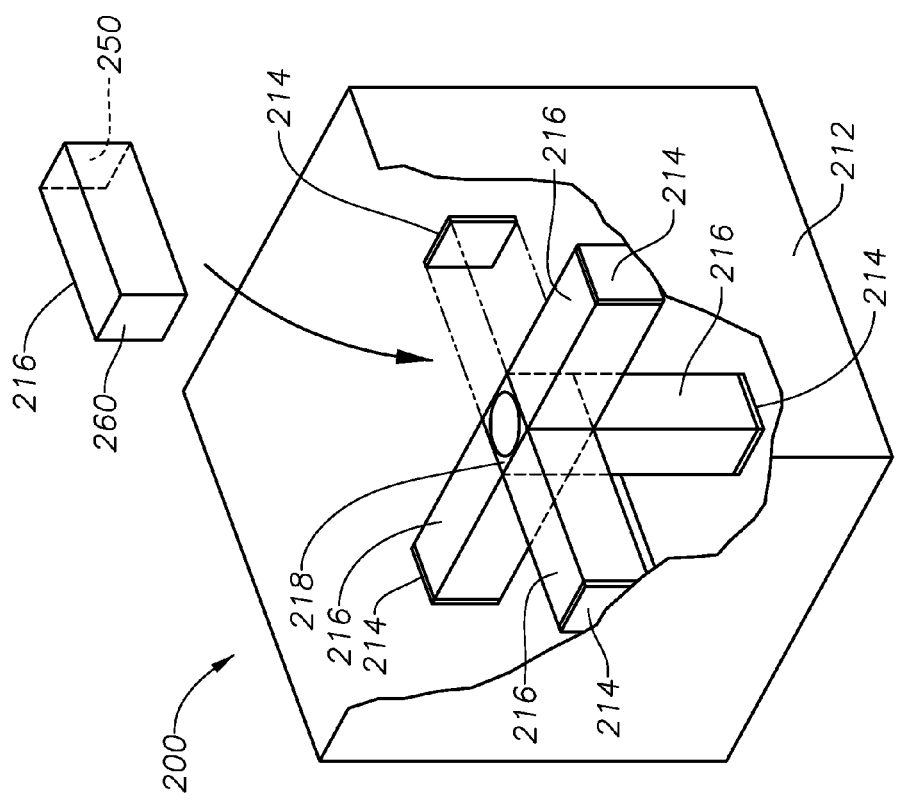
FIG. 5 is a diagrammatical representation of an embodiment of a light source of the present invention for providing enhance LED illumination using blue LED chips.

FIG. 5 is a diagrammatical representation of an embodiment of a light source 200 of the present invention for providing enhance LED illumination using blue LED chips 214. The embodiment of FIG. 5 is substantially identical to the embodiment of FIG. 1 except that LED chips 214 are blue LED chips instead of white LED chips, the proximal face of each light pipe 216 comprises a blue-transmissive, yellow-reflective dichroic coating (mirror) 250 and the distal face of each light pipe 216 comprises a phosphor coating 260. Light source 200 can further comprise a mirror 218, analogous to mirror 18 of FIGS. 1 and 4, and a supporting structure 212.

In operation, each LED chip 214 of light source 200 emits blue light that passes with high efficiency through a blue-transmissive dichroic mirror 250. The transmitted light passing through a mirror 250 is delivered by its corresponding light pipe 216 to a phospor coating 260 at the light pipe 216 distal end. Phosphor coating 260 converts the blue LED light to yellow light by absorbing a portion of the blue light and isotropically re-emitting the absorbed blue light as yellow light, emitting the yellow light in all directions. A portion of this yellow light is emitted backwards through the corresponding light pipe 216 and impinges upon the yellow reflective dichroic coating (mirror) 250 and is substantially reflected by the dichroic coating 250 back towards the phospor coating 260. Because the remotely located phosphor coating 260 at the distal end of each light pipe 216 is cooler and because of the recycled light from the dichroic coating 250, the resultant luminance of each LED chip 214 is greater than that of an LED chip 214 in isolation having a phosphor coating directly on the LED chip 214 output face. As a result, the luminance of light source 200 is greater than the luminance of a single such LED 214 in isolation and light source 200 can provide enhanced LED illumination that can be efficiently coupled to a small diameter target, such as a small diameter optical fiber.

Figure 6:
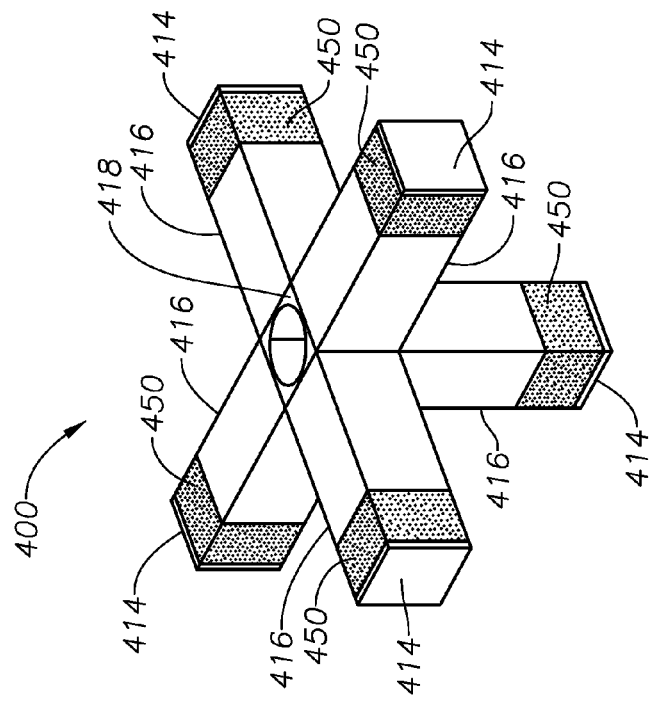
FIG. 6 is a diagrammatical representation of an embodiment of a light source of the present invention comprising silver coated light pipes for preserving luminance of the light source while providing support attachment points.

FIG. 6 is a diagrammatical representation of an embodiment of a light source 400 of the present invention comprising silver coated light pipes 416 for preserving luminance of the light source 400 while providing support attachment points. A dielectric light pipe, such as a light pipe 416, can transmit 100% of internally trapped light from an LED chip 414 via total internal reflection as long as nothing but atmosphere touches the side walls of the light pipe 416. However, as a practical matter it may be necessary to attach supports to the sidewalls of each light pipe 416 to position and hold the light pipe 416 securely in place. Those portions of a light pipe 416 where contact occurs can be coated with a high reflectance (approximately 97-98%) protective coating 450. Coating 450 will enable attachment of mechanical supports to light pipes 416 to secure the light pipes 416 in place with only a slight sacrifice in light transmission. Coating 450 can be, for example, a silver coating or other highly reflective coating as will be known to those having skill in the art. In the embodiment of FIG. 6, a quarter of the length of each light pipe 416 adjacent to each LED chip 414 is coated with coating 450. With the exception of coatings 450, the embodiment of the light source of the present invention of FIG. 6 is substantially identical to the embodiment of FIG. 1 and can also include a mirror 418 identical in function to mirror 18.

In each of the embodiments of the LED light source of the present invention, the light source can be coupled with good thermal contact to a heat sink, as will be known to those having skill in the art. The heat sink can comprise active cooling, such as fan cooling, liquid cooling or thermoelectric cooling. Use of a heat sink as described will enable embodiments of the present invention to maintain cool LED junction temperatures despite the close proximity of the LED chips to one another and to maintain an optical fiber cool despite the close proximity of the optical fiber to the LED chips.

Embodiments of the present invention can also include a method for enhanced LED ophthalmic illumination in accordance with the teachings of the above system and light source embodiments.

Embodiments of this invention can be implemented within a surgical machine or system for use in ophthalmic or other surgery. In particular, it is contemplated that the method and system for enhanced LED illumination of this invention can be implemented in, or incorporated into, any ophthalmic illumination system in which it is desirable to efficiently couple the light from an LED light source to a small diameter optical fiber. Other uses for the method and system of this invention will be apparent to those having skill in the art.

The present invention has been described by reference to certain preferred embodiments; however, it should be understood that it might be embodied in other specific forms or variations thereof without departing from its spirit or essential characteristics. The embodiments described above are therefore considered to be illustrative in all respects and not restrictive, the scope of the invention being indicated by the appended claims.

What is claimed is:

1. An ophthalmic illuminator comprising:
   an illumination source; and
   an optical fiber for transmitting a combined light beam from the illumination source to a site;
   wherein the illumination source comprises:
   a plurality of light emitting diode (LED) chips optically coupled to a corresponding plurality of light pipes, the plurality of LED chips and light pipes arranged in a configuration such that the plurality of light pipes converge together at their distal ends to form a box having five sides formed by the distal ends of the light pipes and an open side from which the combined light beam, composed of light from a plurality of light beams generated by the LED chips and transmitted to the box by the light guides, is emitted.

2. The ophthalmic illuminator of claim 1, wherein a luminance of the combined light beam has a luminance greater than a luminance of any one of the plurality of LED chips.

3. The ophthalmic illuminator of claim 1, wherein the LED chips are high-powered white LED chips.

4. The ophthalmic illuminator of claim 1, wherein the light pipes are square solid light pipes.

5. The ophthalmic illuminator of claim 1, further comprising a mirror having a reflecting surface facing in towards the interior of the box.

6. The ophthalmic illuminator of claim 1, wherein the illumination source further comprises a supporting structure for supporting in place the plurality of LED chips and light pipes.

7. The ophthalmic illuminator of claim 1, wherein the illumination source comprises five LED chips and five corresponding light pipes arranged such that each square light pipe and LED pair is orthogonal to the others.

8. The ophthalmic illuminator of claim 7, wherein the illumination source further comprises a cubical supporting structure to position and hold in place the LED chips and light pipes.

9. The ophthalmic illuminator of claim 1, further comprising a coupling optical component, optically coupled to the plurality of light pipes, for transmitting the combined light beam from the box open side to the optical fiber.

10. The ophthalmic illuminator of claim 1, further comprising an endo-illuminator probe and a connector port for coupling the illumination source to the endo-illuminator probe.

11. The ophthalmic illuminator of claim 1, wherein the site is a surgical site in an eye.

* * * * *